United States Patent [19]

Jaeggi

[11] Patent Number: 4,871,720
[45] Date of Patent: Oct. 3, 1989

[54] AROMATICALLY SUBSTITUTED AZACYCLOALKYL-ALKANEDIPHOSPHONIC ACIDS USEFUL FOR THE TREATMENT OF ILLNESSES THAT CAN BE ATTRIBUTED TO CALCIUM METABOLISM DISORDERS

[75] Inventor: Knut A. Jaeggi, Basel, Switzerland

[73] Assignee: Ciba-Geigy Corporation, Ardsley, N.Y.

[21] Appl. No.: 121,268

[22] Filed: Nov. 16, 1987

[30] Foreign Application Priority Data

Nov. 21, 1986 [CH] Switzerland .................. 4664/86

[51] Int. Cl.$^4$ .................. A61K 31/675; C07F 9/65
[52] U.S. Cl. .................. 514/79; 514/80; 514/82; 514/85; 514/88; 514/89; 514/91; 544/243; 544/337; 540/450; 540/480; 540/481; 540/542; 546/22; 546/23; 546/24; 548/413
[58] Field of Search .............. 540/487, 450, 480, 481, 540/542; 546/22, 23, 24; 548/413; 544/337, 243, 244; 514/80, 85, 89, 91, 79, 82

[56] References Cited

U.S. PATENT DOCUMENTS

| | | | |
|---|---|---|---|
| 4,666,895 | 5/1987 | Bosies et al. .................. | 514/108 |
| 4,687,767 | 8/1987 | Bosies et al. .................. | 514/89 |
| 4,719,203 | 1/1988 | Bosies et al. .................. | 514/108 |
| 4,761,406 | 8/1988 | Flora et al. .................. | 514/86 |

FOREIGN PATENT DOCUMENTS

| | | | |
|---|---|---|---|
| 186405 | 2/1986 | European Pat. Off. . | |
| 3232997 | 3/1984 | Fed. Rep. of Germany . | |
| 0098194 | 7/1980 | Japan .................. | 548/414 |
| 1002300 | 3/1983 | U.S.S.R. .................. | 546/22 |

OTHER PUBLICATIONS

Chem. Abstr. 93: 181017Z (1980), p. 190, Nissan Chem. Ind.
Derwent Abstract 84–010294/02 of Soviet 1002300A (1983).

Primary Examiner—Mukund J. Shah
Assistant Examiner—Diana G. Rivers
Attorney, Agent, or Firm—Irving M. Fishman; JoAnn Villamizar

[57] ABSTRACT

Aromatically substituted azacycloalkylalkanediphosphonic acids of the formula

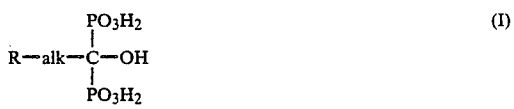

in which R represents an aromatically substituted azacycloaliphatyl radical that is bonded to the group alk by way of a nitrogen atom and that optionally contains an additional nitrogen atom, and alk represents a divalent aliphatic radical, and their salts, can be used for the treatment of illnesses that can be attributed to calcium metabolism disorders. They are manufactured, for example, by reacting a compound of the formula

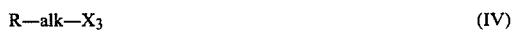

in which $X_3$ represents carboxy, carbamoyl or cyano, with phosphorus acid and phosphorus trichloride and in an intermediate of the formula

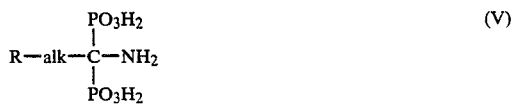

obtained by starting from compounds of the formula IV in which $X_3$ represents cyano or carbamoyl and by working up by hydrolysis, or in a salt thereof, replacing the amino group by hydroxy by treatment with nitrous acid.

21 Claims, No Drawings

AROMATICALLY SUBSTITUTED AZACYCLOALKYL-ALKANEDIPHOSPHONIC ACIDS USEFUL FOR THE TREATMENT OF ILLNESSES THAT CAN BE ATTRIBUTED TO CALCIUM METABOLISM DISORDERS

The invention relates to aromatically substituted azacycloalkylalkanediphosphonic acids of the formula

in which R represents an aromatically substituted azacycloaliphatyl radical that is bonded to the group alk by way of a nitrogen atom and that optionally contains an additional nitrogen atom, and alk represents a divalent aliphatic radical, and their salts, to a process for the manufacture of the compounds according to the invention, to pharmaceutical preparations containing the latter, and to their use as active ingredients in medicaments.

Aromatic substituents R' of mono- or di-azacycloaliphatyl radicals R" are, for example, 5- or 6-membered monocyclic aryl radicals, or bicyclic aryl radicals composed of 5- or 6-membered rings, or 5- or 6-membered monocyclic heteroaryl radicals, or bicyclic heteroaryl radicals composed of 5- or 6-membered rings, which heteroaryl radicals contain as hetero atom(s) 1 or 2 N-atoms, 1 O-atom or S-atom, 1 N-atom and 1 O-atom, or 1 N-atom and 1 S-atom, such as phenyl or, secondly, naphthyl or, thirdly, pyridyl, thienyl or, secondly, pyrimidinyl, quinolinyl, furyl or pyrryl, each of which aryl and heteroaryl radicals is unsubstituted or, especially, is mono- or poly-substituted, preferably mono- or, secondly, di-substituted, by lower alkyl, lower alkoxy and/or by halogen. The mentioned aromatic substituents R' of mono- or di-azacycloaliphatyl radicals R" are bonded to R" preferably by way of a C-atom but may also be bonded to the additional N-atom that may optionally be present.

Mono- or di-azacycloaliphatyl radicals R" are bonded to the radical alk by way of a nitrogen atom (N-atom) and may be substituted, for example by lower alkyl, and/or, as the case may be, bridged, for example by lower alkylene.

As radicals R there may be mentioned especially monocyclic 4- to 8-membered, especially 5- to 8-membered, mono- or di-azacycloalkyl or azacycloalkenyl radicals that are substituted by the group R' and optionally additionally by lower alkyl, or bridged, for example lower-alkylene-bridged, that is to say bicyclic, 4- to 8-membered, especially 5- to 8-membered, mono- or di-azacycloalkyl or azacycloalkenyl radicals that are substituted by the group R' and optionally additionally by lower alkyl, such as pyrrolidino, piperidino, 3,5-methylenepiperidino, i.e. 3-aza-bicyclo[3.1$^{1,5}$.1$^{1,5}$]hept-3-yl, 1,2,5,6-tetrahydropyridino, piperazino, hexahydroazepino, 3-aza-bicyclo[3.2.0$^{1,5}$]hept-3-yl and octahydroazocino radicals. Radicals R are, for example, 3-phenyl- or 3-(p-chlorophenyl)-pyrrolidino, 4-phenyl-, 4-(p-methoxyphenyl)-, 4-(p-methylphenyl)-, 4-(p-chlorophenyl)-, 4-(p-fluorophenyl)- or 4-(m-fluorophenyl)-piperidino, 3-phenyl-3,5-methylenepiperidino, i.e. 1-phenyl-3-aza-bicyclo[3.1$^{1,5}$.1$^{1,5}$]hept-3-yl, 4-(p-chlorophenyl)-3,5-methylene-piperidino, i.e. 6-(p-chlorophenyl)-3-aza-bicyclo[3.1$^{1,5}$.1$^{1,5}$]hept-3-yl, such as exo- or, especially, endo-4-(p-chlorophenyl)-3,5-methylene-piperidino, i.e. exo- or, especially, endo-6-(p-chlorophenyl)-3-aza-bicyclo[3.1$^{1,5}$.1$^{1,5}$]hept-3-yl, also 1-phenyl- or 1-(p-chlorophenyl)-3-aza-bicyclo[3.1$^{1,5}$.1$^{1,5}$]hept-3-yl, 4-phenyl-piperazino, 1-phenyl- or 1-(p-chlorophenyl)-3-aza-bicyclo[3.2.0$^{1,5}$]-hept-3-yl and 4-phenyl-octahydroazocino.

Divalent aliphatic radicals alk are, especially, divalent, lower aliphatic hydrocarbon radicals, such as lower alkylene.

Hereinbelow, there is to be understood by lower radicals and compounds, for example, those containing up to and including 7, especially up to and including 4, C-atoms. In addition, the general terms have, for example, the following meanings:

Lower alkyl is, for example, $C_1$–$C_4$-alkyl, such as methyl, ethyl, propyl, isopropyl or butyl, or also iso-, sec.- or tert.-butyl, but may also be a $C_5$–$C_7$-alkyl group, such as a pentyl, hexyl or heptyl group.

Lower alkoxy is, for example, $C_1$–$C_4$-alkoxy, such as methoxy, ethoxy, propoxy, isopropoxy or butoxy, or also isobutoxy, sec.-butoxy or tert.-butoxy.

Halogen is, for example, halogen having an atomic number of up to and including 35, such as chlorine, or also fluorine or bromine.

Lower alkylene alk is, for example, $C_2$–$C_6$-alkylene, especially straight-chain $C_2$–$C_5$-alkylene, such as ethylene, 1,3-propylene, 1,4-butylene or 1,5-pentylene, or also methylene, 1,2-propylene, 1,2- or 1,3-butylene or 1,4-pentylene, but may also be a hexylene or heptylene group. Lower alkylene as the bridging member of R is, for example, methylene or, secondly, ethylene.

Salts of compounds of the formula I are especially the salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, copper salts, aluminium salts or zinc salts, or ammonium salts with ammonia or organic amines or quaternary ammonium bases, such as optionally C-hydroxylated aliphatic amines, especially mono-, di- or tri-lower alkylamines, for example methyl-, ethyl-, dimethyl- or diethyl-amine, mono-, di- or tri-(hydroxy-lower alkyl)-amines, such as ethanol-, diethanol- or triethanol-amine, tris(hydroxymethyl)amino-methane or 2-hydroxy-tert.-butylamine, or N-(hydroxy-lower alkyl)N,N-di-lower alkylamines or N-(polyhydroxy-lower alkyl)N-lower alkylamines, such as 2-(dimethylamino)-ethanol or D-glucamine, or quaternary aliphatic ammonium hydroxides, for example tetrabutylammonium hydroxide.

The compounds of the formula I and their salts have valuable pharmacological properties. In particular, they exhibit a pronounced regulatory action on the calcium metabolism of warm-blooded animals. In particular, in rats, they bring about pronounced inhibition of bone resorption, which can be demonstrated both in the test procedure according to Acta Endocrinol. 78, 613–24 (1975) by reference to the PTH-induced increase in the serum calcium level after subcutaneous administration in doses of from approximately 0.01 to approximately 1.0 mg/kg, and in the TPTX (thyroparathyroidectomised) rat model by reference to the experimental hypercalcaemia, induced by vitamin $D_3$, after the administration of doses of approximately from 0.001 to 1.0 mg s.c. The tumour hypercalcaemia induced by Walker-256-tumours is likewise inhibited after peroral administration of from approximately 1.0 to approximately 100 mg/kg. Further, in adjuvant arthritis in rats in the test procedure according to Newbould, Brit. J. Pharmacology 21, 127 (1963) and according to Kaibara et al., J. Exp. Med. 159, 1388–96 (1984), they exhibit a marked inhibition of the progression of chronic arthritic processes in doses of approximately from 0.01 to 1.0 mg/kg s.c.. They are therefore excellently suitable as active ingredients in medicaments for the treatment of illnesses that can be attributed to calcium metabolism disorders, for example inflammatory processes in joints and degenerative processes in the arthrodial cartilage, of osteoporosis, periodontitis, hyperparathyroidism and of calcium deposits in blood vessels or on prosthetic implants. A favourable effect is produced both in illnesses in which an anomalous deposition of sparingly soluble calcium salts is to be observed, such as those from among the forms of arthritis, for example Morbus Bechterew, neuritis, bursitis, periodontitis and tendinitis, fibrodysplasia, osteoarthrosis and of artereosclerosis, and in those illnesses in which an anomalous degeneration of hard body tissue is well to the fore, such as hereditary hypophosphatasia, degenerative processes in the arthrodial cartilage, osteoporoses of various origins, Morbus Paget and osteodystrophia fibrosa, and also in tumour-induced osteolytic processes.

The invention relates especially to compounds of the formula I in which R represents a mono- or bicyclic 4- to 8-membered 1-mono- or 1,3-, 1,4- or 1,5-diazacycloalkyl radical R" or a monocyclic 4- to 8-membered azacycloalkenyl radical R" each of which is substituted by a 5- or 6-membered monocyclic aryl radical R' or by a bicyclic aryl radical R' composed of 5- or 6-membered rings, or by a 5- or 6-membered monocyclic heteroaryl radical R' or by a bicyclic heteroaryl radical R' composed of 5- or 6-membered rings, which heteroaryl radicals R' contain as hetero atom(s) 1 or 2 N-atoms, 1 O-atom or S-atom, 1 N-atom and 1 O-atom or 1 N-atom and 1 S-atom, these aryl and heteroaryl radicals R' being unsubstituted or substituted by lower alkyl, lower alkoxy and/or by halogen, and alk represents lower alkylene, and their salts, especially pharmaceutically acceptable salts.

The invention relates, for example, to compounds of the formula I in which R represents a 4- to 8-membered 1-mono- or 1,3-, 1,4- or 1,5-diazacycloalkyl radical R" or a 4- to 8-membered 1-azacycloalkenyl radical R" each of which is substituted by a 5- or 6-membered monocyclic aryl radical R' or by a bicyclic aryl radical R' composed of 5- or 6-membered rings, or by a 5- or 6-membered monocyclic heteroaryl radical R' or by a bicyclic heteroaryl radical R' composed of 5- or 6membered rings, which heteroaryl radicals R' contain as hetero atom(s) 1 or 2 N-atoms, 1 O-atom or S-atom., 1 N-atom and 1 O-atom or 1 N-atom and 1 S-atom, these aryl and heteroaryl radicals R' being unsubstituted or substituted by lower alkyl, lower alkoxy and/or by halogen, and which 4- to 8-membered 1-mono- or 1,3-, 1,4- or 1,5-di-azacycloalkyl radical R" or 4- to 8-membered 1-azacycloalkenyl radical R" may, in addition, be substituted by lower alkyl and/or, as the case may be, bridged by lower alkylene, and alk represents lower alkylene, and their salts, especially pharmaceutically acceptable salts.

The invention relates more especially to compounds of the formula I in which R represents a pyrrolidino, piperidino, piperazino, 3,5-methylenepiperidino, i.e. 3-aza-bicyclo[3.1$^{1,5}$.1$^{1,5}$]hept-3-yl or octahydroazocino radical R" substituted by a phenyl, pyridyl or thienyl radical R' that is unsubstituted or is mono- or di-substituted by $C_1$–$C_4$-alkyl, $C_1$–$C_4$-alkoxy and/or by halogen having an atomic number of up to and including 35, and alk represents straight-chain $C_2$–$C_5$-alkylene, and their salts, especially pharmaceutically acceptable salts.

The invention relates preferably to compounds of the formula I in which R represents a 4-R'-piperidino radical or a 4-R'-3,5-methylene-piperidino, i.e. 6-R'-3-azabicyclo[3.1$^{1,5}$.1$^{1,5}$]hept-3-yl, radical, such as 4-endo-R'-3,5-methylene-piperidino, i.e. 6-endo-R'-3-aza-bicyclo[3.1$^{1,5}$.1$^{1,5}$]hept-3-yl, wherein R' represents unsubstituted phenyl or phenyl substituted by $C_1$–$C_4$-alkyl, $C_1$–$C_4$-alkoxy or by halogen having an atomic number of up to and including 35, and alk represents straight-chain $C_2$–$C_5$-alkylene of the formula —$(CH_2)_n$— wherein n represents an integer from 2 up to and including 5, and their salts, especially pharmaceutically acceptable salts.

The invention relates most especially to compounds of the formula I in which R represents a 3-R'-pyrrolidino or 3- or 4-R'-piperidino radical, wherein R' represents unsubstituted phenyl or phenyl substituted by $C_1$–$C_4$-alkyl, $C_1$–$C_4$-alkoxy or by halogen having an atomic number of up to and including 35, and alk represents straight-chain $C_2$–$C_5$-alkylene of the formula —$(CH_2)_n$— wherein n represents an integer from 2 up to and including 5, and their salts, especially pharmaceutically acceptable salts.

The invention relates specifically to the compounds of the formula I mentioned in the Examples and their salts, especially their internal salts and pharmaceutically acceptable salts with bases.

The invention also relates to a process for the manufacture of compounds of the formula I and their salts, which process is based on methods that are known per se. This process is characterised in that (a) in a compound of the formula

$$\begin{array}{c} X_1 \\ | \\ R-alk-C-OH \\ | \\ X_2 \end{array} \qquad (II)$$

in which $X_1$ represents a functionally modified phosphono group and $X_2$ represents a free or functionally modified phosphono group, $X_1$ and, where appropriate, $X_2$ is(are) converted into the free phosphono group, or (b) a compound of the formula

$$\begin{array}{c} PO_3H_2 \\ | \\ H_2N-alk-C-OH \\ | \\ PO_3H_2 \end{array} \qquad (III)$$

or a salt thereof is reacted with a reactive ester of a corresponding aromatically substituted aliphatic dialcohol, or (c) a compound of the formula

$$R-alk-X_3 \qquad (IV),$$

in which $X_3$ represents carboxy, carbamoyl or cyano, especially carboxy or cyano, is reacted with phosphorous acid and phosphorus trichloride, the primary product is hydrolysed and in an intermediate of the formula

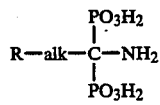

obtained starting from compounds of the formula IV in which $X_3$ represents cyano or carbamoyl, or in a salt thereof, the amino group is replaced by hydroxy by treatment with nitrous acid and, if desired, a resulting compound is converted into a different compound of the formula I and/or a resulting free compound is converted into a salt or a resulting salt is converted into the free compound or into a different salt.

Functionally modified phosphono groups that are to be converted into free phosphono in accordance with process variant a) are, for example, in the form of an ester, especially in the form of a diester of the formula $-P(=O)(OR)_2$ (IIa) wherein OR represents, for example, lower alkoxy, or a phenoxy group that is optionally substituted by lower alkyl, lower alkoxy, halogen, trifluoromethyl and/or by hydroxy.

The conversion of a functionally modified phosphono group into a free phosphono group is effected in customary manner by hydrolysis, for example in the presence of a mineral acid, such as hydrochloric or sulphuric acid, or by reaction with a tri-lower alkylhalosilane, for example trimethyldichlorosilane or especially trimethyliodosilane or trimethylbromosilane, preferably while cooling, for example in a temperature range of from approximately 0° to approximately 25° C.

The starting materials of the formula II can be manufactured, for example, by reacting a compound of the formula $$R-alk-COOH \quad (IIb)$$

or preferably the anhydride or acid chloride thereof with a corresponding phosphorous acid triester of the formula $P(OR)_3$ (IIc) in the presence of a tri-lower alkylamine, for example triethylamine, to form a compound of the formula

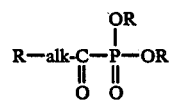

and further reacting the latter with a phosphorous acid diester of the formula $H-P(=O)(OR)_2$ (IIe) or $P(OH)(OR)_2$ (IIf) in the presence of a di-lower alkylamine, for example diethylamine, or in the presence of an alkali metal lower alkoxide, for example sodium methoxide, to form the corresponding compound of the formula

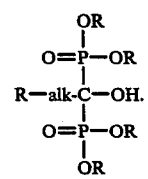

Starting materials of the formula IIb can, if they are not known, be manufactured, for example, by reacting a corresponding compound of the formula $$R-H \quad (IIh)$$

with a compound of the formula $$Y-alk-COOR \quad (IIi)$$

in which Y is halogen, such as bromine, or, for the manufacture of compounds IIb in which alk represents $C_2-C_7$-alkylene of which the free valencies extend from adjacent C-atoms, for example ethylene, with a compound of the formula $$alk'-COOR \quad (IIj)$$

in which alk' represents a $C_2-C_7$-alkenyl radical, and by hydrolysing the ester obtained in each case to the acid and anhydridising or chlorinating the latter, for example by means of phosphorus pentachloride.

Starting materials IIh can in their turn be obtained by reacting with each other, in customary manner, compounds of the formulae $$R'-M \text{ (IIk) and } O=R'''-X' \quad (III),$$

in which M represents a metal radical, such as an alkali metal atom, for example a lithium atom, or a halo-magnesium group, for example a bromomagnesium group, R''' represents the divalent azacycloaliphatyl radical that corresponds to the radical R'' and is bonded to the oxo group by way of the bonding site provided for R', and X' represents an amino-protecting group, such as α-aryl-, α,α-diaryl or α,α,α-triaryl-lower alkyl, for example benzyl, or tri-lower alkylsilyl, for example trimethylsilyl, and by removing the elements of water from the resulting compound of the formula

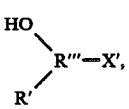

for example by acid treatment, and in the resulting compound of the formula $$R-X' \quad (IIn),$$

which is mono-unsaturated in the α,β-position to the radical R', removing the amino-protecting group, for example by hydrogenolysis in the case of α-aryl, α,α-diaryl- and α,α,α-triaryl-lower alkyl and, for example, by hydrolysis in the case of α,α,α-triaryllower alkyl and tri-lower alkylsilyl, and, if desired, hydrogenating the double bond to a single bond.

Compounds IIh in which R represents a 3-R'-pyrrolidino radical that is optionally lower alkylated in the 2-, 3- and/or 4-position can also be manufactured in an especially elegant manner by reacting a corresponding 3-R'-lower alk-2-enecarboxylic acid ester with a nitrolower alkane, hydrogenating the nitro group in the resulting 3-R'-3-(1-nitro-lower alkyl)-lower alkanecarboxylic acid ester to the amino group, as a result of which ring closure to form the corresponding 3-R'-pyrrolidin-5-one takes place, and replacing the oxo group by hydrogen by means of reduction, for example by treatment with lithium aluminium hydride or diborane.

Reactive mono- or di-esters of aromatically substituted aliphatic dialcohols that are to be used in accordance with process variant (b) are, for example, the hydrohalic acid esters, such as hydrochloric, hydrobromic or hydriodic acid esters, thereof, the sulphonic acid esters, such as alkane- or optionally substituted benzene-sulphonic acid esters, thereof, such as the methane- or p-toluene-sulphonates thereof, or the sulphuric acid esters thereof.

The reaction with the mentioned reactive diesters of aromatically substituted aliphatic dialcohols is effected, for example, in the presence of a base, such as an alkali metal or alkaline earth metal hydroxide, for example sodium hydroxide, or a quaternary ammonium hydroxide, for example tetrabutylammonium hydroxide, advantageously in the presence of a solvent or diluent.

The starting materials of the formula III can be manufactured, for example, by reacting a compound of the formula $$H_2N-alk-COOH \qquad (IIIa)$$

in customary manner, for example in chlorobenzene, with phosphorous acid and phosphorus trichloride and then working up by hydrolysis.

In a modification of process variant (b), a compound of the formula III can also be condensed with a reactive mono- or di-ester of an aliphatic alcohol that is aromatically substituted by R', and the primary product of the formula

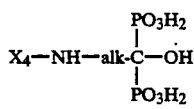

in which $X_4$ represents R'-aliphatyl substituted by optionally reactively esterified hydroxy, can be cyclised.

The reaction of compounds of the formula IV with phosphorous acid and phosphorus trichloride in accordance with process variant (c) is effected in customary manner, the phosphorous acid component preferably being formed in situ by reaction of excess phosphorus trichloride with water-containing phosphoric acid, for example with commercially customary approximately 75% to 95%, preferably approximately 85%, phosphorus acid. The reaction is advantageously carried out while heating, for example at from approximately 70° to approximately 120° C., in a suitable solvent, such as tetrachloroethane, trichloroethane, chlorobenzene, chlorotoluene or paraffin oil, and with working up being effected by hydrolysis.

The treatment of intermediates of the formula V with nitrous acid is effected in customary manner with the latter being freed in aqueous solution from one of its salts, for example sodium nitrite, by acid treatment, for example by the action of hydrochloric acid, during which a corresponding, unstable diazonium salt, for example diazonium chloride, is formed as intermediate, which diazonium salt, with the introduction of the α-hydroxy group, splits off nitrogen.

The starting materials of the formula IV can, if they are not known, be manufactured, for example, by reacting a corresponding compound of the formula $$R-H \qquad (IIh)$$

with a compound of the formula $$Y-alk-X_3 \qquad (IIi)$$

in which Y is halogen, such as bromine, or, for the manufacture of compounds of the formula IV in which alk represents $C_2$–$C_7$-alkylene of which the free valencies extend from adjacent C-atoms, for example ethylene, with a compound of the formula $$alk'-X_3 \qquad (IIf)$$

in which alk' represents a $C_2$–$C_7$-alkenyl radical, and, if desired, in each case hydrolysing the resulting primary product to the acid.

Compounds of the formula I obtained in accordance with the process of the invention or in accordance with another process that is known per se can be converted in a manner known per se into other compounds of the formula I.

For example, the radical R' can be substituted, for example halogen can be introduced by reaction with a customary nuclear halogenating agent, for example with chlorine or bromine in the presence of a Lewis acid, such as iron(III) trichloride.

Depending on the starting materials and procedures chosen, the novel compounds may be in the form of one of the possible isomers or in the form of a mixture thereof, for example depending on the number of asymmetric carbon atoms, they may be in the form of pure optical isomers, such as antipodes, or in the form of isomeric mixtures, such as racemates, diastereoisomeric mixtures or mixtures of racemates.

Resulting diastereoisomeric mixtures and mixtures of racemates can be separated in known manner into the pure isomers, diastereoisomers or racemates on the basis of the physico-chemical differences between the components, for example by chromatography and/or fractional crystallisation.

Resulting racemates can also be resolved according to known methods into the optical antipodes, for example by recrystallisation from an optically active solvent, with the aid of microorganisms, or by reaction of an acid end product with an optically active base that forms salts with the racemic acid and by separation of the salts obtained in that manner, for example on the basis of their differing solubilities, into the diastereoisomers from which the antipodes can be freed by the action of suitable agents. Advantageously, the more active of the two antipodes is isolated.

Resulting free compounds of the formula I, including their internal salts of the formula I, can be converted into salts with bases by partial or complete neutralisation with one of the bases mentioned at the beginning. Acid addition salts also can be converted in an analogous manner into the corresponding free compounds or internal salts thereof.

Conversely, resulting free compounds of the formula I can be converted into acid addition salts by treatment with one of the protonic acids mentioned at the beginning.

Resulting salts can be converted into the free compounds in a manner known per se, for example by treatment with an acid reagent, such as a mineral acid, or, as the case may be, with a base, for example alkali liquor.

The compounds, including their salts, may also be obtained in the form of their hydrates or may include the solvent used for crystallisation.

Owing to the close relationship between the novel compounds in free form and in the form of their salts, hereinbefore and hereinafter there is to be understood by the free compounds or their salts, where appropriate and expedient, optionally also the corresponding salts or free compounds, respectively.

The invention relates also to those embodiments of the process according to which a compound obtainable as an intermediate at any stage of the process is used as starting material and the remaining steps are carried out or a starting material in the form of a salt and/or racemate or antipode is used or especially is formed under the reaction conditions.

The starting materials that are used in the process of the present invention are preferably those which result in the compounds described at the beginning as being especially valuable. The invention relates also to novel starting materials and processes for the manufacture thereof.

The pharmaceutical preparations according to the invention, which contain compounds of the formula I or pharmaceutically acceptable salts thereof, are for enteral, such as oral or rectal, and parenteral administration and contain the pharmacological active ingredient on its own or together with a pharmaceutically acceptable carrier.

The novel pharmaceutical preparations contain, for example, from approximately 10% to approximately 80%, preferably from approximately 20% to approximately 60%, active ingredient. Pharmaceutical preparations according to the invention for enteral and parenteral administration are, for example, those in dosage unit form, such as dragées, tablets, capsules or suppositories, and also ampoules. These are prepared in a manner known per se, for example by means of conventional mixing, granulating, confectioning, dissolving or lyophilising processes. For example, pharmaceutical preparations for oral administration can be obtained by combining the active ingredient with solid carriers, if desired granulating a resulting mixture and, if desired or necessary, processing the mixture or granulate, after the addition of suitable adjuncts, into tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatine, tragacanth, methylcellulose and/or polyvinylpyrrolidone, and/or, if desired, disintegrators, such as the above-mentioned starches, carboxymethyl starch, crosslinked polyvinylpyrrolidone, agar, alginic acid or a salt thereof, such as sodium alginate. Adjuncts are especially flow-regulating and lubricating agents, for example silica, talc, stearic acid or salts thereof, such as magnesium or calcium stearate, and/or polyethylene glycol. Dragée cores are provided with suitable coatings which may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures, or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules consisting of gelatine, and also soft sealed capsules consisting of gelatine and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, it being possible also to add stabilisers.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatine rectal capsules that contain a combination of the active ingredient with a base material; suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, or suspensions of the active ingredient, such as corresponding oily injection suspensions, in which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran and, if desired, also stabilisers.

The present invention relates also to the use of the compounds of the formula I and their salts, preferably for the treatment of illnesses that can be attributed to calcium metabolism disorders, for example of the rheumatic type, and especially of osteoporoses.

Dosages under 0.01 mg/kg body weight have only a negligible effect on pathological calcification or the degeneration of hard tissue. At dosages above 100 mg/kg body weight, toxic side-effects may occur in long-term use. The compounds of the formula I and their salts can be administered both orally and, in the form of a hypertonic solution, subcutaneously, intramuscularly or intravenously. The preferred daily doses are in the range of approximately from 0.1 to 5 mg/kg in the case of oral administration, in the range of approximately from 0.1 to 1 mg/kg in the case of subcutaneous and intramuscular administration and in the range of approximately from 0.01 to 2 mg/kg, for example approximately from 0.013 to 0.67 mg/kg, in the case of intravenous administration.

The dosage of the compounds used is, however, variable and depends on the particular conditions, such as nature and severity of the illness, duration of treatment and on the particular compound. Single doses contain, for example, from 0.01 to 10 mg, dosage unit forms for parenteral, such as intravenous, administration contain, for example, from 0.01 to 0.1 mg, preferably 0.02 to 0.08 mg, and oral dosage unit forms contain, for example, from 0.2 to 2.5 mg, preferably from 0.3 to 1.5 mg, per kg of body weight. The preferred individual dosage for oral administration is from 10 to 100 mg and for intravenous administration from 0.5 to 5 mg and can be administered up to 4 times per day. The higher dosages in the case of oral administration are necessary owing to the limited resorption. In the case of long-term treatments, the initially higher dosage can normally be converted to low dosages while still maintaining the desired effect.

The following Examples illustrate the invention described above; they are not intended, however, to limit the scope thereof in any way. Temperatures are given in degrees Celsius.

EXAMPLE 1

26.98 g (0.1 mol) of 3-(4-phenylpiperidino)propionic acid hydrochloride are heated at 100° under reflux, while stirring, with 13.4 ml of 85% phosphoric acid and 50 ml of chlorobenzene. Then, at 100°, 27 ml of phosphorus trichloride are added dropwise, gas evolution taking place. A thick mass separates out of the reaction mixture over the course of 30 minutes. Heating is continued for a further 3 hours at 100° and the supernatant chlorobenzene is then decanted off. The viscous mass remaining behind is boiled under reflux for 3 hours, while stirring, with 100 ml of 9N hydrochloric acid. The reaction mixture is filtered while hot with the addition of carbon and the filtrate is diluted with acetone, the 3-(4-phenylpiperidino)-1-hydroxy-propane-1,1-diphosphonic acid separating out in crystalline form; m.p. 243°-245° (decomposition) (yield 57% of the theoretical yield).

The 3-(4-phenylpiperidino)propionic acid hydrochloride used as starting material can be manufactured in the following manner:

25.0 g of 4-phenylpiperidine (0.15 mol) are placed in 50 ml of diethyl ether and, while stirring, 15.1 g of ethyl acrylate are gradually added thereto. With a slight increase in temperature, a clear solution forms. After standing overnight at room temperature, the ether is distilled off. The oil remaining behind is the crude 3-(4-phenylpiperidino)-propionic acid ethyl ester (yield approx. 95%).

39.4 g of 3-(4-phenylpiperidino)-propionic acid ethyl ester are heated under reflux with 600 ml of 4N hydrochloric acid for 24 hours. The reaction mixture is then fully concentrated by evaporation under reduced pressure and the crystalline residue is triturated with acetone. After filtering off the crystals with suction and washing and drying them, 3-(4-phenylpiperidino)propionic acid hydrochloride, m.p. 216°-217°, is obtained. (Yield 90% of the theoretical yield).

EXAMPLE 2

In a manner analogous to that described in Example 1 it is possible to manufacture, starting from 0.1 mol in each case of 3-(3-phenylpyrrolidino)propionic acid hydrochloride;
3-[4-(p-methoxyphenyl)piperidino]propionic acid hydrochloride;
3-[4-(p-chlorophenyl)piperidino]propionic acid hydrochloride;
3-[4-(p-fluorophenyl)piperidino]propionic acid hydrochloride;
4-(4-phenylpiperidino)butyric acid hydrochloride and
6-(4-phenylpiperidino)hexanoic acid hydrochloride, also 3-(3-phenylpyrrolidino)-1-hydroxy-propane-1,1-diphosphonic acid, m.p. 221° (decomposition);
3-[4-(p-methoxyphenyl)piperidino]-1-hydroxy-propane-1,1-diphosphonic acid, m.p. 243°-245° (decomposition);
3-[4-(p-chlorophenyl)piperidino]-1-hydroxy-propane-1,1-diphosphonic acid;
3-[4-(p-fluorophenyl)piperidino]-1-hydroxy-propane-1,1-diphosphonic acid;
4-(4-phenylpiperidino)-1-hydroxy-butane-1,1-diphosphonic acid, m.p. 230° (decomposition) and
6-(4-phenylpiperidino)-1-hydroxy-hexane-1,1-diphosphonic acid, m.p. 236°-237° (decomposition), respectively, and the salts thereof, for example the disodium salts.

The 4-(4-phenylpiperidino)butyric acid hydrochloride and the 6-(4-phenylpiperidino)hexanecarboxylic acid hydrochloride used as starting materials can be manufactured as follows:

1.61 g (0.01 mol) of 4-phenylpiperidine, 2.76 g of potassium carbonate and 2.15 g of bromobutyric acid ethyl ester are heated under reflux, while stirring, in 20 ml of 2-butanone for 24 hours. The inorganic salts are then filtered off with suction and the filtrate is concentrated by evaporation. After boiling the residue, crude 4-(4-phenylpiperidino)butyric acid ethyl ester, for 24 hours with 40 ml of 4N hydrochloric acid and subsequently concentrating by evaporation, triturating with acetone and filtering off the crystals with suction, 4-(4-phenylpiperidino)butyric acid hydrochloride, m.p. 217°-220° (decomposition) is obtained.

The 6-(4-phenylpiperidino)hexanecarboxylic acid hydrochloride, m.p. 197°-198°, is obtained analogously using 6-bromohexanecarboxylic acid ethyl ester.

In an analogous manner, there are obtained from
3-phenylpyrrolidine;
4-(4-methoxyphenyl)piperidine;
4-(4-chlorophenyl)piperidine and
4-(4-fluorophenyl)piperidine;
by reaction with acrylic acid ester and subsequent hydrolysis with hydrochloric acid,
3-(3-phenylpyrrolidino)propionic acid hydrochloride, m.p. 139°-140°;
3-[4-(4-methoxyphenyl)piperidino]-propionic acid hydrochloride, m.p. 214° (decomposition);
3-[4-(4-chlorophenyl)piperidino]-propionic acid hydrochloride; and
3-[4-(4-fluorophenyl)piperidino]-propionic acid hydrochloride, respectively.

EXAMPLE 3

In a manner analogous to that described in Example 1, it is possible to manufacture, starting from
4-(p-methylphenyl)piperidine;
4-(2-thienyl)piperidine;
4-(3-thienyl)piperidine;
4-(3-pyridyl)piperidine;
4-(4-pyridyl)piperidine;
4-(2-pyridyl)piperidine;
4-phenyl-octahydro-azocine and
4-endo-(p-chlorophenyl)-3,5-methylenepiperidine, i.e. 6-endo-(p-chlorophenyl)-3-aza-bicyclo[3.1$^{1,5}$.1$^{1,5}$-]heptane, via
3-[4-(p-methylphenyl)piperidino]propionic acid hydrochloride;
3-[4-(2-thienyl)piperidino]propionic acid hydrochloride;

3-[4-(3-thienyl)piperidino]propionic acid hydrochloride;

3-[4-(3-pyridyl)piperidino]propionic acid hydrochloride;

3-[4-(4-pyridyl)piperidino]propionic acid hydrochloride;

3-[4-(2-pyridyl)piperidino]propionic acid hydrochloride;

3-(4-phenyl-octahydro-azocino)propionic acid hydrochloride and

3-[4-endo-(p-chlorophenyl)-3,5-methylene-piperidino]-propionic acid hydrochloride, i.e. 3-[6-endo-(p-chlorophenyl)-3-aza-bicyclo[3.1$^{1,5}$.1$^{1,5}$]hept-3-yl]propionic acid hydrochloride, m.p. 220°, respectively 3-[4-(p-methylphenyl)piperidino]-1-hydroxy-propane-1,1-diphosphonic acid;

3-[4-(2-thienyl)piperidino]-1-hydroxy-propane-1,1-diphosphonic acid;

3-[4-(3-thienyl)piperidino]-1-hydroxy-propane-1,1-diphosphonic acid;

3-[4-(3-pyridyl)piperidino]-1-hydroxy-propane-1,1-diphosphonic acid;

3-[4-(4-pyridyl)piperidino]-1-hydroxy-propane-1,1-diphosphonic acid;

3-[4-(2-pyridyl)piperidino]-1-hydroxy-propane-1,1-diphosphonic acid;

3-(4-phenyl-octahydro-azocino)-1-hydroxy-propane-1,1-diphosphonic acid and

3-[4-endo-(p-chlorophenyl)-3,5-methylene-piperidino]-1-hydroxy-propane-1,1-diphosphonic acid, i.e. 3-[6-endo(p-chlorophenyl)-3-aza-bicyclo[3.1$^{1,5}$.1$^{1,5}$]hept-3-yl]-1-hydroxy-propane-1,1-diphosphonic acid, m.p. 224° (decomposition), respectively, and the salts thereof, for example the disodium salts.

The endo-6-(p-chlorophenyl)-3-aza-bicyclo[3.1$^{1,5}$.1$^{1,5}$]heptane (hydrochloride) to be used as starting material can be manufactured in the following manner:

(a) 49 g of tri-n-butyltin hydride are added under a nitrogen atmosphere to a solution of 72 g of endo-1-bromo-6-(p-chlorophenyl)-3-(p-methoxybenzyl)-3-azabicyclo[3.1$^{1,5}$.1$^{1,5}$]heptane-2,4-dione and 1.65 g of bisazoisobutyronitrile in 1.66 liters of tetrahydrofuran. The reaction solution is heated under reflux for 1 hour and then concentrated. The crystals so obtained are worked up as described in Example 4d1). Endo-6-(p-chlorophenyl)-3-(4-methoxybenzyl)-3-aza-bicyclo[3.1$^{1,5}$.1$^{1,5}$]heptane-2,4-dione is obtained in the form of white crystals of m.p. 156°-158°.

(b) A solution of 280 g of cerium(IV) ammonium nitrate in 390 ml of water is added dropwise at room temperature to a stirred suspension of 47.7 g of endo-6-(p-chlorophenyl)-3-(p-methoxybenzyl)-3-aza-bicyclo[3.1$^{1,5}$.1$^{1,5}$]—heptane-2,4-dione in 0,5 liter of acetonitrile. When the addition is complete, the reaction mixture is stirred for 4 hours at room temperature, 200 ml of acetonitrile are distilled therefrom under a water-jet vacuum and then the reaction mixture is diluted with 800 ml of water. It is stirred for 1 hour in an ice bath and filtered with suction. The resulting light yellow crystals are washed with water and ether. The intermediate is dissolved in 1 liter of methylene chloride, 6.8 g of n-propylamine are added thereto and the whole is left to stand overnight. Filtration is then carried out and the light brown solution is concentrated to 70 ml. It is diluted with 70 ml of ether and filtered with suction. The resulting grey-brown, crystalline endo-6-(p-chlorophenyl)-3-aza-bicyclo[3.1$^{1,5}$.1$^{1,5}$]heptane-2,4-dione is washed with 50 ml of methylene chloride/ether (1:1); m.p. 227°-228°.

(c) 5.9 g of endo-6-(p-chlorophenyl)-3-aza-bicyclo[3.1$^{1,5}$.1$^{1,5}$]heptane-2,4-dione are reacted in 130 ml of toluene with 24 ml of sodium dihydrobis-(2-methoxyethoxy)-aluminate-toluene solution (70%; FLUKA) and worked up with 24 ml of concentrated sodium hydroxide solution analogously to Example 4d2). Endo-6-(p-chlorophenyl)-3-aza-bicyclo[3.1$^{1,5}$.1$^{1,5}$]heptane hydrochloride is obtained in the form of white crystals of m.p. 236°-237°.

EXAMPLE 4:

In a manner analogous to that described in Examples 1 and 2, it is possible to manufacture, starting from 4-(m-fluorophenyl)piperidine;

1-phenylpiperazine;

3-(p-chlorophenyl)pyrrolidine;

3-phenylpyrrolidine;

6-exo-(p-chlorophenyl)-3-aza-bicyclo[3.1$^{1,5}$.1$^{1,5}$]heptane and 1-phenyl-3-aza-bicyclo[3.1$^{1,5}$.1$^{1,5}$]heptane via 3-[4-(m-fluorophenyl)piperidino]propionic acid hydrochloride, m.p. 207°-208°;

3-(4-phenylpiperazino)propionic acid hydrochloride, m.p. 206°-207°;

3-[3-(p-chlorophenyl)pyrrolidino]propionic acid hydrochloride, m.p. 201°;

3-(3-phenylpyrrolidino)propionic acid hydrochloride, m.p. 139°-140°;

3-[6-exo-(p-chlorophenyl)-3-aza-bicyclo[3.1$^{1,5}$.1$^{1,5}$]hept-3-yl]propionic acid hydrochloride, m.p. 232° and 3-(1-phenyl-3-aza-bicyclo[3.1$^{1,5}$.1$^{1,5}$]hept-3-yl)propionic acid hydrochloride, m.p. 139°-140°, respectively, 3-[4-(m-fluorophenyl)piperidino]-1-hydroxy-propane-1,1-diphosphonic acid, m.p. 239°-240° (decomposition);

3-(4-phenylpiperazinyl)-1-hydroxy-propane-1,1-diphosphonic acid, m.p. 234° (decomposition);

3-[3-(4-chlorophenyl)pyrrolidinyl]-1-hydroxy-propane-1,1-diphosphonic acid, m.p. 219° (decomposition);

3-(3-phenylpyrrolidino)-1-hydroxy-propane-1,1-diphosphonic acid, m.p. 221° (decomposition);

3-[6-exo-(p-chlorophenyl)-3-aza-bicyclo[3.1$^{1,5}$.1$^{1,5}$]hept-3-yl]-1-hydroxy-propane-1,1-diphosphonic acid, m.p. 236°, and 3-(1-phenyl-3-aza-bicyclo[3.1$^{1,5}$.1$^{1,5}$]hept-3-yl)-1-hydroxy-propane-1,1-diphosphonic acid, m.p. 252° (decomposition), respectively, and the salts thereof, for example the disodium salts.

The exo-6-(p-chlorophenyl)-3-aza-bicyclo[3.1$^{1,5}$.1$^{1,5}$]heptane (hydrochloride) to be used as starting material can be manufactured in the following manner:

(a1) 131.6 g of N-(4-methoxybenzyl)-4-chlorocinnamic acid amide are added, while stirring, to a stirred suspension of 100 g of phosphorus pentachloride in 2 liters of benzene. The reaction mixture is then stirred for 30 minutes at room temperature and then for 30 minutes at 50°. After concentrating, the dark brown oil is taken up in 600 ml of toluene and concentrated. The residue is dissolved in 1.2 liters of carbon tetrachloride, diatomaceous earth (HYFLO-Super-Cel ®) is added thereto, and the product is filtered off, concentrated by evaporation and dried in vacuo.

The resulting orange, crystalline intermediate is dissolved in 1.2 liters of methylene chloride and added dropwise to a solution of 430 ml of N sodium hydrogen carbonate solution, 6.2 g of tetra-n-butylammonium bromide and 600 ml of water. When the addition is complete, 100 ml of N sodium hydrogen carbonate solution are added dropwise and the whole is then stirred for 2 hours. The organic phase is separated off and the aqueous phase is extracted twice with methylene chloride. The combined organic phases are dried over magnesium sulphate and concentrated, and the crude product is dried under a high vacuum. 4-aza-2-bromo-7-(p-chlorophenyl)-4-(4-methoxybenzyl)-1,6-heptadiene-3,5-dione is obtained in the form of a dark brown oil and is further reacted immediately.

(b1) A solution of 111.8 g of 4-aza-2-bromo-7-(4-chlorophenyl)-4-(4-methoxybenzyl)-1,6-heptadiene-3,5-dione and 0.6 g of 2,6-di-tert.-butyl-p-cresol in 1.4 liters of xylene is heated under reflux for 2 hours. After cooling, the dark brown precipitate is separated from the black reaction solution, stirred with ether, filtered off with suction and washed with ether. Fractional crystallisation from acetonitrile yields first exo-1-bromo-6-(4-chlorophenyl)-3-(4-methoxybenzyl)-3-aza-bicyclo[3.1$^{1,5}$.1$^{1,5}$]heptane-2,4-dione in the form of light yellow crystals having a melting point of 177°–180° C. and, as a second product, the diastereoisomeric compound endo-1-bromo-6-(p-chlorophenyl)-3-(p-methoxybenzyl)-3-aza-bicyclo[3.1$^{1,5}$.1$^{1,5}$]heptane-2,4-dione of m.p. 142.5°–143.5°.

(c1) A solution of 249 g of cerium(IV) ammonium nitrate in 330 ml of water is added dropwise at room temperature to a stirred suspension of 52.1 g of exo-1-bromo-6-(p-chlorophenyl)-3-(4-methoxybenzyl)-3-azabicyclo[3.1$^{1,5}$.1$^{1,5}$]heptane-2,4-dione in 2.1 liters of acetonitrile. When the addition is complete, the reaction mixture is stirred at room temperature for 1 hour, is heated to 40°, the resulting solution is allowed to cool slowly to room temperature again and is stirred for a further 3 hours. It is concentrated to a third of its volume and then diluted with 1.6 liters of water. The product which precipitates is filtered off with suction, washed with water, ether and ethyl acetate and dried in vacuo. Exo-1-bromo-6-(p-chlorophenyl)-3-aza-bicyclo[3.1$^{1,5}$.1$^{1,5}$]heptane-2,4-dione is obtained in the form of yellow crystals of m.p. 231°–232°.

(d1) 60 g of tri-n-butyltin hydride are added under a nitrogen atmosphere to a solution of 58.5 g of exo-1-bromo-6-(p-chlorophenyl)-3-aza-bicyclo[3.1$^{1,5}$.1$^{1,5}$]-heptane-2,4-dione and 1.9 g of bisazoisobutyronitrile in 1 liter of tetrahydrofuran. The reaction solution is heated under reflux for 4 hours and then concentrated in vacuo. The crystalline residue is taken up in cyclohexane, filtered off with suction and washed with ether. Exo-6-(p-chlorophenyl)-3-aza-bicyclo[3.1$^{1,5}$.1$^{1,5}$]heptane-2,4-dione is obtained in the form of white crystals of m.p. 179°–181°.

(e) 3.5 g of exo-6-(p-chlorophenyl)-3-aza-bicyclo[3.1$^{1,5}$.1$^{1,5}$]heptane-2,4-dione in 75 ml of toluene are reacted with 24 ml of sodium dihydrobis(2-methoxyethoxy)-aluminate-toluene solution (70%; FLUA) and worked up with 24 ml of concentrated sodium hydroxide solution (see paragraph bridging pages 32 and 33). Exo-6-(p-chlorophenyl)-3-aza-bicyclo[3.1$^{1,5}$.1$^{1,5}$ ]heptane hydrochloride of m.p. 201°–203° is obtained.

The 1-phenyl-3-aza-bicyclo[3.1$^{1,5}$.1$^{1,5}$]heptane (hydrochloride) to be used as starting material can be manufactured in the following manner:

(a2) A solution of 103 ml of oxalyl chloride in 400 ml of methylene chloride is added dropwise over a period of 2½ hours at room temperature to a stirred solution of 88.8 g of 2-phenylacrylic acid in 7 ml of dimethylformamide and 1.6 liters of methylene chloride. When the addition is complete, the whole is stirred for 2 hours and then concentrated by evaporation in vacuo. The brown, oily product is taken up in 600 ml of ether and separated from the viscid residue, filtered over diatomaceous earth (HYFLO-Super-Cel®) and concentrated in vacuo. The brown oil is dissolved in 0.8 liter of methylene chloride and added dropwise to a solution, cooled to 0° to 5°, of 95.6 g of N-(p-methoxybenzyl)acrylamide, 6.43 g of 4-dimethylaminopyridine and 63.1 g of triethylamine in 1 liter of methylene chloride. When the addition is complete, the whole is stirred for 3 hours at room temperature. After concentrating the reaction solution to 250 ml by evaporation, 1 liter of ether is added. The organic phase is decanted from the viscid residue. The residue is taken up in 500 ml of ether three times and the organic phase is decanted each time. The combined organic phases are concentrated to 200 ml and filtered over HYFLO-Super-Cel® (see above). Concentration to dryness by evaporation yields 4-aza-4-(4-methoxybenzyl)-2-phenyl-1,6-heptadiene-3,5-dione in the form of a brown oil. The latter is further reacted immediately.

(b2) A solution of 65.7 g of 4-aza-4-(p-methoxybenzyl)-2-phenyl-1,6-heptadiene-3,5-dione and 0.5 g of 2,6-ditert.-butyl-p-cresol in 1 liter of 1,3-dichlorobenzyl is stirred at 170° for 6 hours. After concentrating by evaporation, the residue is chromatographed over 2.5 kg of silica gel using toluene/ether (9:1). The resulting brown oil is dissolved at 70° in 550 ml of diisopropyl ether and cooled in an ice bath while stirring. The precipitate is filtered off with suction. After drying under a high vacuum, 3-(4-methoxybenzyl)-1-phenyl-3-aza-bicyclo[3.1$^{1,5}$.1$^{1,5}$]heptane-2,4-dione is obtained in the form of white crystals of m.p. 87°–88°.

(c2) A solution of 344 g of cerium(IV) ammonium nitrate in 1.1 liter of acetonitrile is added dropwise at room temperature to a stirred solution of 53 g of 3-(4-methoxybenzyl)-1-phenyl-3-aza-bicyclo[3.1$^{1,5}$.1$^{1,5}$]-heptane-2,4-dione in 560 ml of acetonitrile. After 1 hour, 515 ml of water are added and the whole is stirred for 2 hours. By distilling off acetonitrile the reaction solution is concentrated to half its volume and is then diluted with 1 liter of water. The resulting product is filtered off with suction, washed with water and dried in vacuo. The brown-yellow, crystalline substance is taken up in 800 ml of methylene chloride, 11 ml of n-propylamine are added thereto and the whole is left to stand overnight. The black solution is concentrated, 80 ml of methylene chloride/ether (1:1) are added to the brown, crystalline mass and the product is filtered off with suction and dried under a high vacuum. 1-phenyl-3-aza-bicyclo[3.1$^{1,5}$.1$^{1,5}$]heptane-2,4-dione is obtained in the form of white crystals of m.p. 217°–218°.

(d2) 25.5 ml of sodium dihydrobis-(2-methoxyethoxy)aluminate-toluene solution (70%; FLUKA) are added dropwise under a nitrogen atmosphere to a stirred suspension of 3 g of 1-phenyl-3-aza-bicyclo[3.1$^{1,5}$.1$^{1,5}$]heptane-2,4-dione in 150 ml of toluene. During the addition, the temperature is maintained in the range of from 25° to 35° by external cooling in an ice bath. When the addition is complete, the reaction mixture is stirred for 15 minutes at room temperature and then heated under reflux for 1 hour. After cooling in an ice bath, 25.5 ml of concentrated sodium hydroxide solution are added dropwise at from 10° to 15°. The organic phase is decanted and the aqueous phase is washed with toluene.

The combined organic phases are washed twice with 100 ml of water and once with 70 ml of saturated sodium chloride solution. After the addition of magnesium sulphate, the organic phase is filtered and concentrated under a water-jet vacuum. The brownish oil is dissolved in 50 ml of ether. By introducing hydrogen chloride, the 1-phenyl-3-aza-bicyclo[3.1$^{1,5}$.1$^{1,5}$]heptane hydrochloride is obtained in the form of a crystalline product which, after being filtered off with suction, is again suspended in ether and again filtered off with suction and finally dried overnight under a high vacuum: white crystals of m.p. 248°–249°.

EXAMPLE 5

Tablets, each containing 75 mg of active ingredient, for example 3-(4-phenylpiperidino)-1-hydroxy-propane-1,1-diphosphonic acid or a salt, for example the sodium salt, thereof, can be prepared in the following manner:
Constituents (for 1000 tablets)
active ingredient 75.0 g
lactose 268.5 g
corn starch 22.5 g
polyethylene glycol 6000 5.0 g
talc 15.0 g
magnesium stearate 4.0 g
demineralised water q.s.
Preparation: The solid ingredients are first forced through a sieve of 0.6 mm mesh width. Then the active ingredient, the lactose, the talc, the magnesium stearate and half of the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed to form tablets of approximately 10 mm diameter which are concave on both sides and have a breaking notch on the upper side.

In an analogous manner, it is also possible to prepare tablets each containing 75 mg of another of the compounds of the formula I mentioned in Examples 1 to 4, which compounds may also be in the form of salts with bases, for example in the form of the disodium salt.

EXAMPLE 6

Tablets, each containing 10 mg of active ingredient, for example 3-(4-phenylpiperidino)-1-hydroxy-propane-1,1-diphosphonic acid or a salt, for example the sodium salt, thereof, can be prepared in the following manner:
Composition (for 1000 tablets)
active ingredient 10.0 g
lactose 328.5 g
corn starch 17.5 g
polyethylene glycol 6000 5.0 g
talc 25.0 g
magnesium stearate 4.0 g
demineralised water q.s.
Preparation: The solid ingredients are first forced through a sieve of 0.6 mm mesh width. Then the active ingredient, the lactose, the talc, the magnesium stearate and half of the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed to form tablets of approximately 10 mm diameter which are concave on both sides and have a breaking notch on the upper side.

In an analogous manner, it is also possible to prepare tablets each containing 10 mg of another compound of the formula I mentioned in Examples 1 to 4, which compound may also be in the form of a salt with a base, for example in the form of the disodium salt.

EXAMPLE 7

Gelatine dry-filled capsules, each containing 100 mg of active ingredient, for example 3-(4-phenylpiperidino)-1-hydroxy-propane-1,1-diphosphonic acid or a salt, for example the sodium salt, thereof, can be prepared in the following manner:
Composition (for 1000 capsules)
active ingredient 350.0 g
microcrystalline cellulose 30.0 g
sodium lauryl sulphate 2.0 g
magnesium stearate 8.0 g
The sodium lauryl sulphate is sieved into the active ingredient (lyophilised) through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm mesh width and, after mixing for a further 3 minutes, the mixture is introduced in portions of 390 mg each into size 0 (elongated) gelatine dry-fill capsules.

In an analogous manner, it is also possible to prepare capsules each containing 100 mg of another compound of the formula I according to Examples 1 to 4, which compound may also be in the form of a salt with a base, for example in the form of the disodium salt.

EXAMPLE 8

A 0.2% injection or infusion solution can be prepared, for example, in the following manner:
active ingredient, for example 3-(4-phenylpiperidino)-1-hydroxy-propane-1,1-diphosphonic acid or a salt, for
example the sodium salt, thereof 5.0 g
sodium chloride 22.5 g
phosphate buffer pH 7.4 300.0 g
demineralised water to 2500.0 ml
The active ingredient is dissolved in 1000 ml of water and filtered through a microfilter. The buffer solution is added and the whole is made up to 2500 ml with water. To prepare dosage unit forms, portions of 1.0 or 2.5 ml each are introduced into glass ampoules (each containing respectively 2.0 or 5.0 mg of active ingredient).

I claim:

1. An aromatic substituted azacycloaliphatic diphosphonic acid of the formula

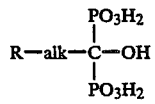
(I)

wherein R denotes a pyrrolidino piperidino, 1,2,5,6-tetrahydropyridino, piperazino, hexahydroazepino, 3-aza-bicyclo(3.1$^{1,5}$.1$^{1,5}$)hept-3-yl, 3-aza-bicyclo(3.2.0$^{1,5}$)hept-3-yl or octahydroazocino radical R″ each of which is substituted by a phenyl, naphthyl, pyrryl, furyl, thienyl, pyridyl, pyrimidinyl or quinolynl group $R_{,}$, these groups R, being unsubstituted or substituted by one or two substituents selected from the group consisting of lower alkyl, lower alkoxy and halogen and alk represents a $C_2$–$C_6$alkylene or a pharmaceutically acceptable salt thereof.

2. A compound claimed in claim 1, in which R is a pyrrolidino, piperidino, piperazino, 3-aza-bicyclo[$3.1^{1,5}.1^{1,5}$]hept-3-yl or octahydroazocino group R″ substituted by a phenyl, pyridyl or thienyl radical R, that is unsubstituted or is mono- or di-substituted by substituents being selected from the group consisting of $C_1$–$C_4$-alkyl, $C_1$–$C_4$-alkoxy and halogen having an atomic number of up to and including 35, and alk is a straight-chain $C_2$–$C_5$-alkylene, or a pharmaceutically acceptable salt thereof.

3. A compound claimed in claim 1, in which R is a 4-R′-piperidino or 6-R′-3aza-bicyclo[$3.1^{1,5}.1^{1,5}$]-hept-3yl group, wherein $R_{,}$ is phenyl or phenyl substituted by $C_1$–$C_4$alkyl, $C_1$–$C_4$-alkoxy or by halogen having an atomic number of up to and including 35, and alk is a straight-chain $C_2$–$C_5$-alkylene of the formula —(CH$_2$)— wherein n is an integer from 2 up to an including 5, or a pharmaceutically acceptable salt thereof.

4. A compound claimed in claim 1, in which R is a 3-R′-pyrrolidino or 3— or 4-R′-piperidino group, wherein R′ is phenyl or phenyl substituted by $C_1$–$C_4$-alkyl, $C_1$–$C_4$-alkoxy or by halogen having an atomic number of up to and including 35, and alk is a straight-chain $C_2$–$C_5$-alkylene of the formula —(CH$_2$)$_n$— wherein n represents an integer from 2 up to and including 5, or a pharmaceutically acceptable salt thereof.

5. A compound claimed in claim 1 being 3-(4-phenyl-piperidino)-1-hydroxy-propane-1,1-diphosphonic acid or a pharmaceutically acceptable salt thereof.

6. A compound claimed in claim 1 being 3-(3-phenyl-pyrrolidino)-1-hydroxy-propane-1,1-diphosphonic acid or a pharmaceutically acceptable salt thereof.

7. A compound claimed in claim 1 being 3-[4-(p-methoxyphenyl)piperidino]1-hydroxy-propane-1,1-diphosphonic acid or a pharmaceutically acceptable salt thereof.

8. A compound claimed in claim 1 being 3-[4-(p-chlorophenyl)piperidino]1-hydroxy-propane-1,1-diphosphonic acid or a pharmaceutically acceptable salt thereof.

9. A compound claimed in claim 1 being 3-[4-fluorophenyl)piperidino]-1-hydroxy-propane-1,1-diphosphonic acid or a pharmaceutically acceptable salt thereof.

10. A compound claimed in claim 1 being 3-[6-endo(p-chlorophenyl)-3-aza-bicyclo-[$3.1^{1,5}.1^{1,5}$]hept-3-yl]-1-hydroxy-propane-1,1-diphosphonic acid or a pharmaceutically acceptable salt thereof.

11. A compound claimed in claim 1 being 4-(4-phenylpiperidino)-1-hydroxy-butane-1,1-diphosphonic acid or a pharmaceutically acceptable salt thereof.

12. A compound claimed in claim 1 being 6-(4-phenylpiperidino)-1-hydroxy-hexane-1,1-diphosphonic acid or a pharmaceutically acceptable salt thereof.

13. A compound claimed in claim 1 being 3-[4(p-methylphenyl)piperidino[-1-hydroxy-propane-1,1-diphosphonic acid or a pharmaceutically acceptable salt thereof.

14. A compound claimed in claim 1 being 3-(4-phenyl-octahydro-azocino)-1-hydroxy-propane-1,1-diphosphonic acid or a pharmaceutically acceptable salt thereof.

15. A compound claimed in claim 1 being 3-[4-(m-fluorophenyl)piperidino)-1-hydroxy-propane-1,1-diphosphonic acid or a pharmaceutically acceptable salt thereof.

16. A compound claimed in claim 1 being 3-(4-phenylpiperazino)-1-hydroxy-propane,1,1-diphosphonic acid or a pharmaceutically acceptable salt thereof.

17. A compound claimed in claim 1 being 3-[3-(p-chlorophenyl)pyrrolidino]-1-hydroxy-propane-1,1-diphosphonic acid or a pharmaceutically acceptable salt thereof.

18. A compound claimed in claim 1 being 3-[6-exo(p-chlorophenyl)-3-aza-bicyclo-[$3.1^{1,5}.1^{1,5}$]hept-3-yl]-1 -hydroxy-propane-1,1-diphosphonic acid or a pharmaceutically acceptable salt thereof.

19. A compound claimed in claim 1 being 3-(1-phenyl-3-aza-bicyclo[$3.1^{1,5}.1^{1,5}$]hept-3-yl)-1-hydroxypropane-1,1-diphosphonic acid or a pharmaceutically acceptable salt thereof.

20. A pharmaceutical composition for the treatment of illnesses that can be attributed to calcium metabolism disorders, consisting of a therapeutically effective amount of a compound according to claim 1 and one or more pharmaceutically acceptable carriers.

21. A method for the treatment of illnesses that can be attributed to calcium metabolism disorders, wherein a therapeutically effective amount of a compound according to claim 1 or a pharmaceutically acceptable salt thereof is administered to a warm-blooded organism in need of such treatment.

* * * * *